United States Patent
Yih et al.

(10) Patent No.: US 8,084,242 B2
(45) Date of Patent: Dec. 27, 2011

(54) METHODS AND MEDIUMS FOR CULTIVATING DINOPHYSIS ACUMINATA

(75) Inventors: Won Ho Yih, Daejeon (KR); Hyung Seop Kim, Jeonbuk (KR); Myung Gil Park, Gwangju (KR); Jung-rae Rho, Gunsan-si (KR)

(73) Assignees: Industry-Academic Cooperation Foundation, Gunsan-Si (KR); Kunsan National University, Gunsan-Si (KR)

( * ) Notice: Subject to any disclaimer, the term of this patent is extended or adjusted under 35 U.S.C. 154(b) by 1148 days.

(21) Appl. No.: 11/849,973

(22) Filed: Sep. 4, 2007

(65) Prior Publication Data

US 2008/0102513 A1     May 1, 2008

(30) Foreign Application Priority Data

Nov. 1, 2006    (KR) .......................... 10-2006-0107494

(51) Int. Cl.
    *C12N 1/00*    (2006.01)
    *C12N 1/10*    (2006.01)
(52) U.S. Cl. ...................... 435/243; 435/258.1; 435/947
(58) Field of Classification Search ........................ None
    See application file for complete search history.

(56) References Cited

U.S. PATENT DOCUMENTS

2008/0102513 A1*   5/2008   Yih et al. ................... 435/258.1
2010/0105928 A1*   4/2010   Yih et al. ..................... 549/263

* cited by examiner

*Primary Examiner* — Debbie K Ware
(74) *Attorney, Agent, or Firm* — Joseph Hyosuk Kim; JHK Law (57) ABSTRACT

Disclosed are a method and a medium for cultivating the marine dinoflagellate *Dinophysis acuminata*. The laboratory culture of *D. acuminata* causing diarrhetic shellfish poisoning, whose cultivation was known difficult, has been first established, thereby contributing to a better understanding of ecophysiology, biology and toxicology of *Dinophysis* species, as well as the evolution of dinoflagellate plastids.

5 Claims, 9 Drawing Sheets

METHODS AND MEDIUMS FOR CULTIVATING DINOPHYSIS ACUMINATA

TECHNICAL FIELD

The present invention relates to a method and a medium for cultivating *Dinophysis acuminata*, a marine dinoflagellate, and more specifically, to the method and the medium for cultivating *Dinophysis acuminata* with supplying *Myrionecta rubra*, a marine ciliate, as prey.

Background Art

The marine dinoflagellate genus *Dinophysis* includes both phototrophic and heterotrophic species and is globally distributed in coastal and oceanic waters. Cell abundances of *Dinophysis* species are usually low (<100 cells·l$^{-1}$), but at times they form seasonal blooms with a few thousand cells per liter in some areas of Europe and Japan. *Dinophysis* species are of economic and public importance as they cause diarrhetic shellfish poisoning and have a significant effect on shellfish industries in many parts of the world because of the threat to human health after consumption of contaminated shellfish. Nonetheless, despite considerable efforts since the early work [Barker H. A. (1935) The culture and physiology of the marine dinoflagellates, Arch. Mikrobiol. 6:157-181], all attempts to cultivate *Dinophysis* sp. have failed. Further detailed exploration of the ecophysiology, life history, toxicology, plastid evolution, etc. of the *Dinophysis* species has been hampered by an inability to culture them. Therefore, our current knowledge about *Dinophysis* species has been derived only from natural populations.

Photosynthetic species of *Dinophysis* do not survive when cultured in various media that support growth of many other phytoplankton species. Microscopic observations show that photosynthetic species often contain food vacuoles, reflecting mixotrophy, indicating that 'feeding' may be necessary for successful culture of *Dinophysis* species. However, despite the supply of potential prey organisms, including cryptophytes *Teleaulax* sp. [Nishitani G. et al. (2003) Trying to cultivation of *Dinophysis caudata* (Dinophyceae) and the appearance of small cells, Plankton Biol. Ecol. 50:31-36], all attempts to cultivate members of the genus *Dinophysis* have failed.

Dinoflagellates possess 5 different types of plastids, and have acquired and lost them many times during their evolution. *Dinophysis* species are known to possess plastids of cryptophyte origin, the way in which they enter *Dinophysis* cells has not yet been confirmed. Like *Dinophysis acuminata*, *M. rubra* contains plastids of cryptophyte origin. The origin of the plastids has been proposed to be via kleptoplasitidy following the ingestion of cryptophyte. Recent morphological and experimental evidences, however, suggest that *M. rubra* does not acquire chloroplasts from its cryptophyte prey, and rather it feeds on cryptophytes in order to gain an essential growth factor for continued growth.

Disclosure of the Invention

The present inventors have first established a method for cultivating *Dinophysis* sp., which could not have been cultivated in laboratory, and further tried to identify feeding mechanism, growth rate and evolution of plastids, using the culture.

Therefore, it is an object of the present invention to provide a method for cultivating *Dinophysis acuminata*.

It is another object of the present invention to provide a culture medium for *Dinophysis acuminata*.

One aspect of the present invention relates to a method for cultivating *Dinophysis acuminata*, comprising the step of cultivating *Dinophysis acuminata* in a seawater medium at a temperature of 10~30° C. under continuous light with supplying *Myrionecta rubra* as prey.

In the method of the present invention, it is preferred not to supply *Teleaulax* sp. The seawater medium can be any conventional culture medium for algae except diatoms, for example, f/2-Si medium, particularly, 30 psu (practical salinity unit) f/2-Si medium. In the method of the present invention, the initial density ratio (cell number·ml$^{-1}$) of *Dinophysis acuminata* to *Myrionecta rubra* is preferably 1:1~10, more preferably 1:3~7, and most preferably 1:5. The cultivation is preferably performed at a temperature of 15~25° C., particularly 20° C. and under continuous light of 50~70 μmol photon·m$^{-2}$·s$^{-1}$, particularly 60 μmol photon·m$^{-2}$·s$^{-1}$.

Another aspect of the present invention relates to a culture medium for *Dinophysis acuminata* comprising:
 (i) a seawater medium; and
 (ii) *Myrionecta rubra* as prey.

The medium of the present invention preferably contains no *Teleaulax* sp. The seawater medium can be any conventional culture medium for algae except diatoms, for example, f/2-Si medium, particularly, 30 psu (practical salinity unit) f/2-Si medium. The initial density ratio (cell number·ml$^{-1}$) of *Dinophysis acuminata* to *Myrionecta rubra* is preferably 1:1~10, more preferably 1:3~7, and most preferably 1:5.

Hereinafter, the present invention will be described in detail.

The present inventors have first established a method for cultivating *Dinophysis acuminata* belonging to marine dinoflagellates *Dinophysis* sp. including several species that cause diarrhetic shellfish poisoning, none of which has been established in culture, and further identified feeding mechanism, growth rate and evolution of plastids of this species, using the culture.

According to the present invention, *D. acuminata* grew well in laboratory culture when supplied with *M. rubra*, a marine ciliate, as prey (growth rate: 0.95 d$^{-1}$), reaching a maximum cell density of approximately 2,400 cells·ml$^{-1}$ at the end of the feeding experiment. By contrast, when *M. rubra* was not supplied as prey or *Teleaulax* sp. was supplied in place of *M. rubra*, *D. acuminata* did not grow continuously. *D. acuminata* uses a peduncle to extract the cell contents of *M. rubra*. The laboratory culture of *D. acuminata* established according to the present invention was confirmed maintained for a long time using *M. rubra* as prey.

When both *M. rubra* and *Teleaulax* sp. were supplied as prey, the cell number of *D. acuminata* was increased initially but gradually decreased thereafter. One plausible reason could be that the growth of *D. acuminata* was inhibited by the competition for nutrients or allelopathy from *Teleaulax* sp. Another plausible reason could be that the three species have different pH limits for growth. That is, *Teleaulax* sp. may have a higher pH limit for growth than *M. rubra* or *D. acuminata*, and thus, the latter two species may reach their pH limits for growth before *Teleaulax* sp.

BEST MODE FOR CARRYING OUT THE INVENTION

Hereinafter, the present invention will be specifically explained with reference to the following Examples and Comparative Examples. However, it will be appreciated that those skilled in the art, on consideration of this disclosure, may make modifications and improvements within the spirit and scope of the present invention.

Herein, "day(s)" is abbreviated to "d," "hour(s)" to "h," and "minute(s)" to "m," respectively.

EXAMPLE 1

Cultivation of Dinophysis Acuminata

Dinophysis acuminata was established in culture by isolating single cell from seawater samples collected in Masan Bay, Korea (128° 34' E, 35° 12' N) on Dec. 20, 2005. The Dinophysis culture was grown in 30 psu f/2-Si medium at 20° C. under continuous light (60 μmol photons·m$^{-2}$·s$^{-1}$) with addition of the marine ciliate Myrionecta rubra (strain MR-MAL01) as the prey species every 2 to 3 d. Cultures of M. rubra were grown using the cryptophyte Teleaulax sp. (strain CR-MAL01) as prey, as described in [Yih W et al. (2004) Ingestion of cryptophyte cells by the marine photosynthetic ciliate Mesodinium rubrum. Aquat. Microb. Ecol. 36:165-170]. The cryptophyte culture was grown under the same conditions described above. All of the 3 cultures were non-axenic. The f/2-Si medium was prepared based on f/2 medium excluding $Na_2SiO_3·9H_2O$.

| <f/2 medium> | |
|---|---|
| $NaNO_3$ (75.0 g/l d$H_2O$) | 1.0 ml |
| $NaH_2PO_4·H_2O$ (5.0 g/l d$H_2O$) | 1.0 ml |
| $Na_2SiO_3·9H_2O$ (30.0 g/l d$H_2O$) | 1.0 ml |
| f/2 trace metal solution | 1.0 ml |
| f/2 vitamin solution | 1.0 ml |
| Filtered seawater | ad 1.0 l |
| <f/2 trace metal solution> | |
| $FeCl_3·6H_2O$ | 3.15 g |
| $Na_2EDTA·2H_2O$ | 4.36 g |
| $CuSO_4·5H_2O$ (9.8 g/l d$H_2O$) | 1.0 ml |
| $Na_2MoO_4·2H_2O$ (6.3 g/l d$H_2O$) | 1.0 ml |
| $ZnSO_4·7H_2O$ (22.0 g/l d$H_2O$) | 1.0 ml |
| $CoCl_2·6H_2O$ (10.0 g/l d$H_2O$) | 1.0 ml |

| -continued | |
|---|---|
| $MnCl_2·4H_2O$ (180.0 g/l d$H_2O$) | 1.0 ml |
| Distilled water | ad 1.0 l |
| <f/2 vitamin solution> | |
| Vitamin $B_{12}$ (1.0 g/l d$H_2O$) | 1.0 ml |
| Biotin (1.0 g/l d$H_2O$) | 10.0 ml |
| Thiamine HCl | 200 mg |
| Distilled water | ad 1.0 l |

A dense culture of Dinophysis acuminata in exponential growth was split into 3 aliquots and diluted with fresh medium to prepare triplicate 300 ml bottles for each of 3 experimental treatments. One set of treatment bottles received M. rubra as prey for D. acuminata. Initial concentrations of D. acuminata and M. rubra were 100 and 500 cells·ml$^{-1}$, respectively. All bottles were incubated at 20° C. under continuous light (60 μmol photons·m$^{-2}$·s$^{-1}$) for 7 d. Daily subsamples were fixed with acid Lugol's solution and cells were enumerated using a Sedgewick-Rafter chamber.

Figure 1A:
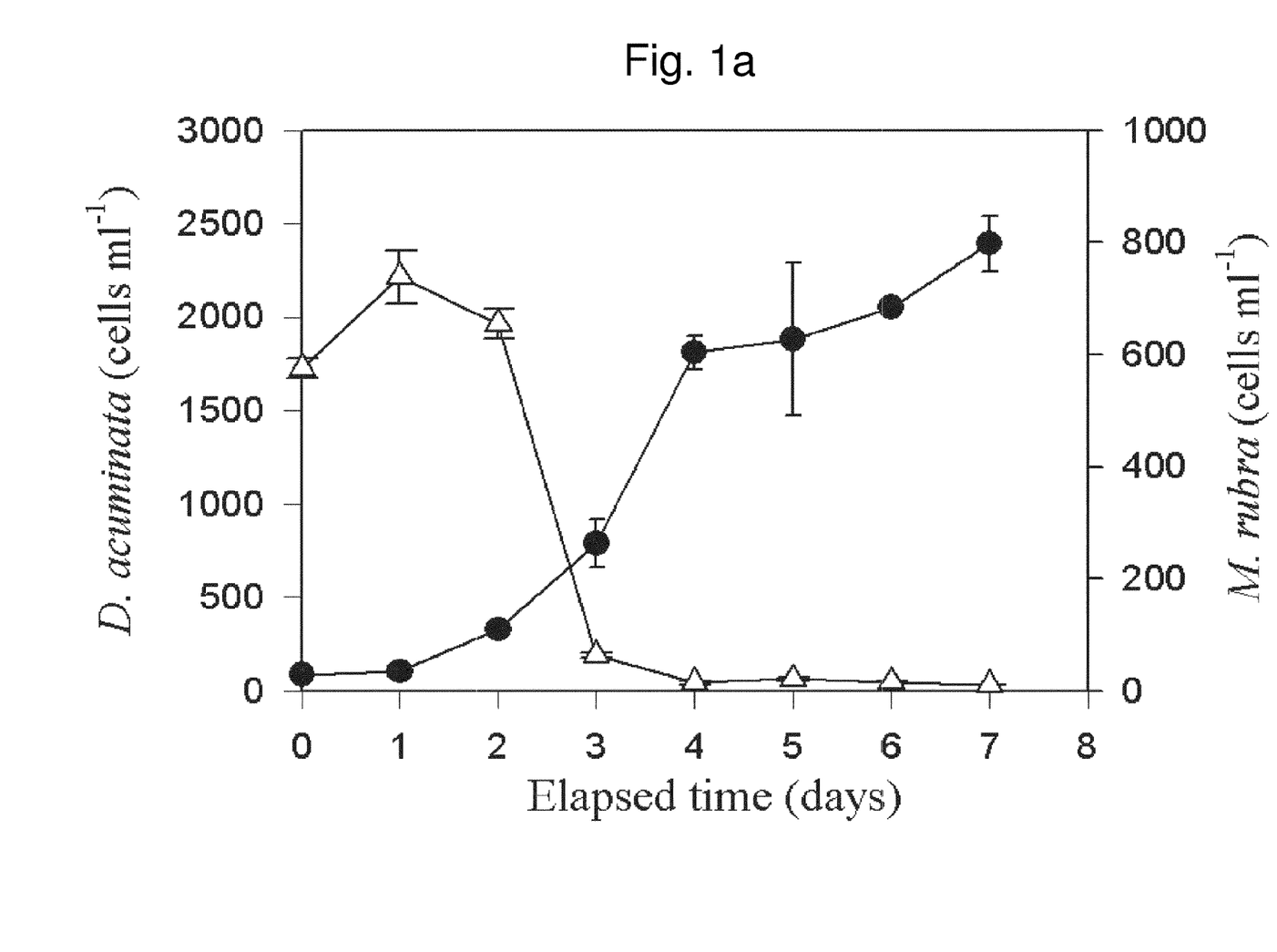
Fig. 1a is a graph showing changes in cell numbers of *D. acuminata* (—●—; the same hereunder) and *M. rubra* Δ; the same hereunder) in cultures of *D. acuminata* supplied with *M. rubra* as prey.
Figure 1B:
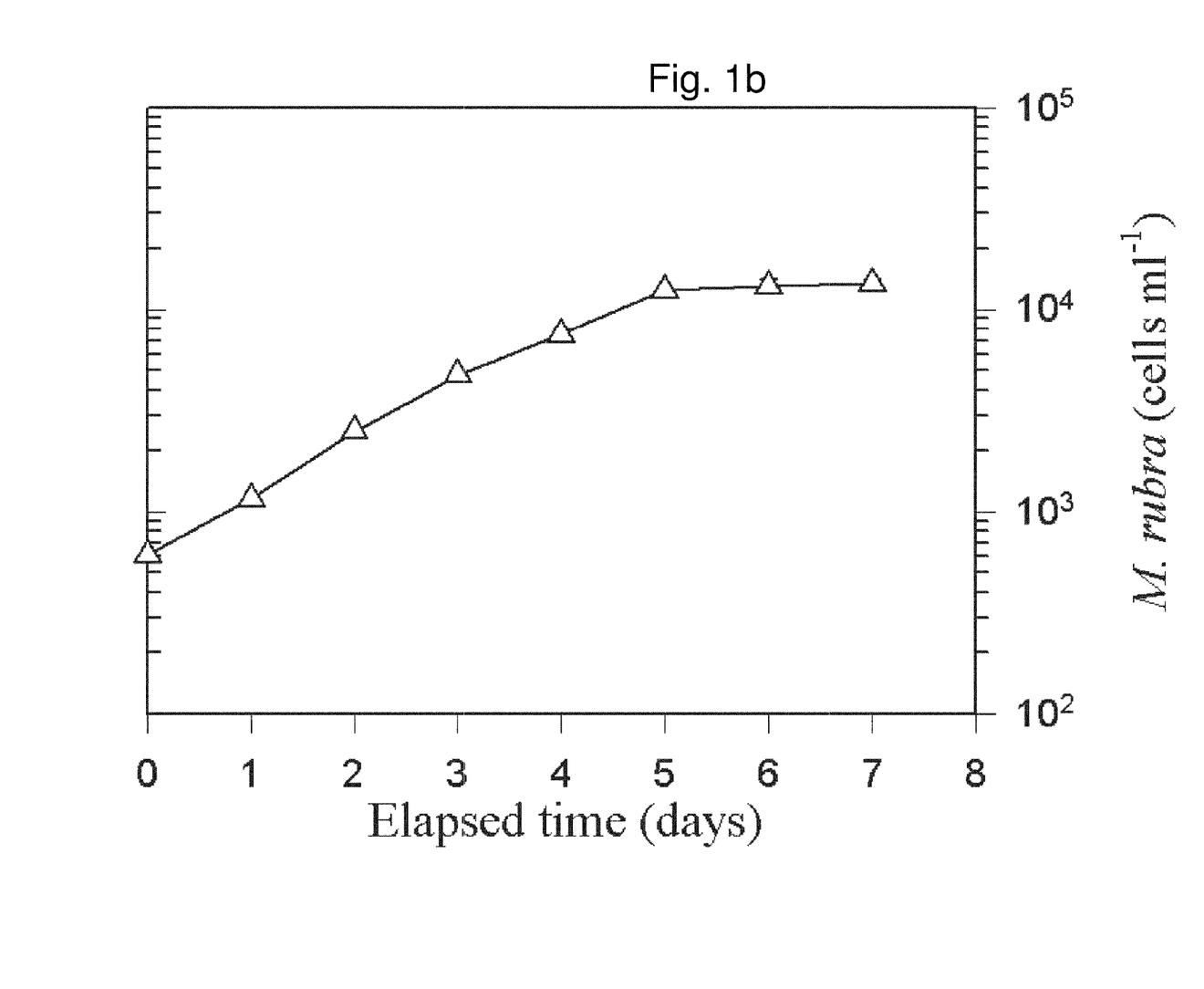
FIG. 1b is a graph showing change in cell number of *M. rubra* in cultures of *M. rubra* alone.
Figure 1C:
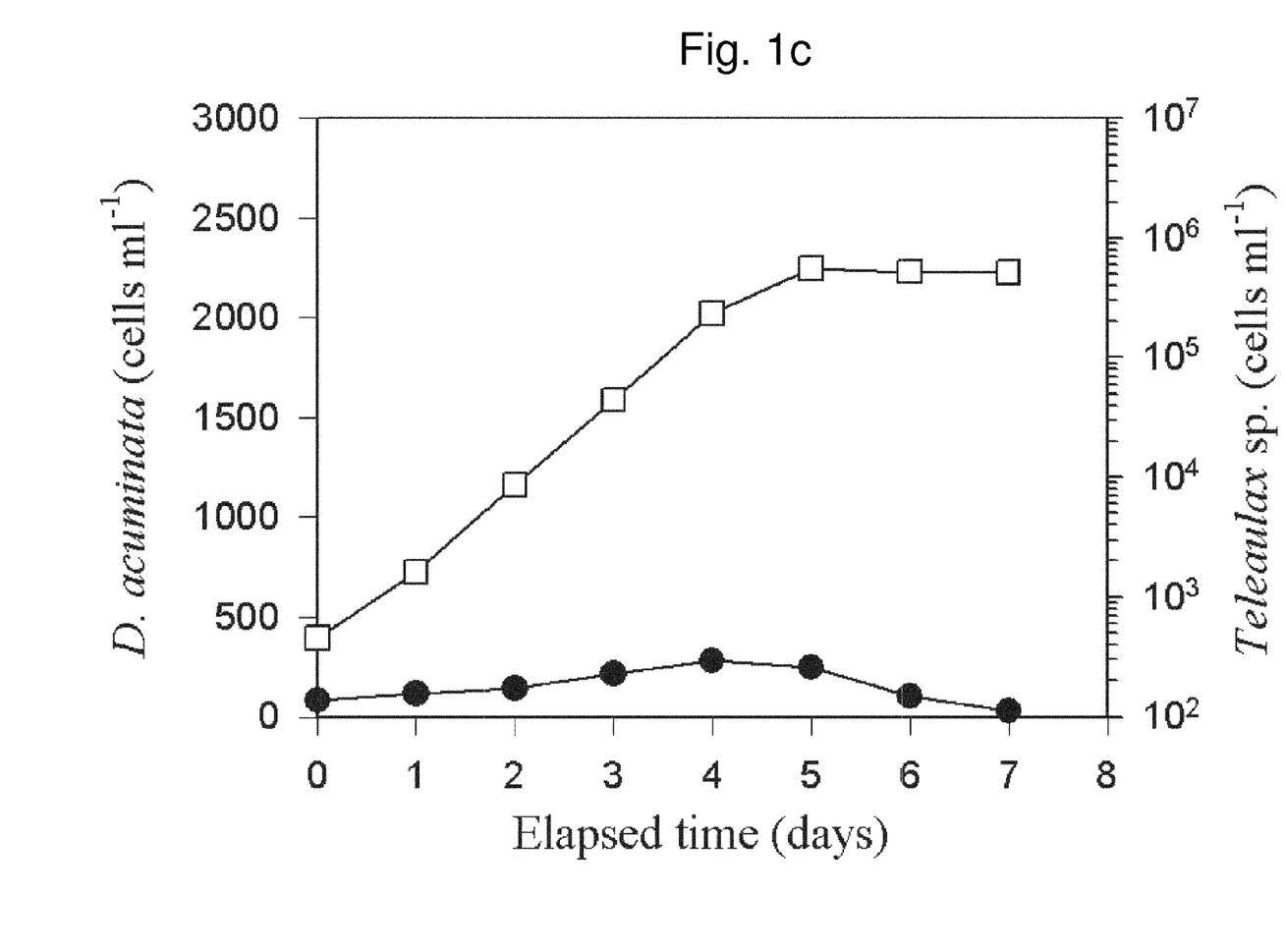
FIG. 1c is a graph showing changes in cell numbers of D. acuminata and Teleaulax sp. (—□—; the same hereunder) in cultures of D. acuminata supplied with Teleaulax sp. as prey.
Figure 1D:
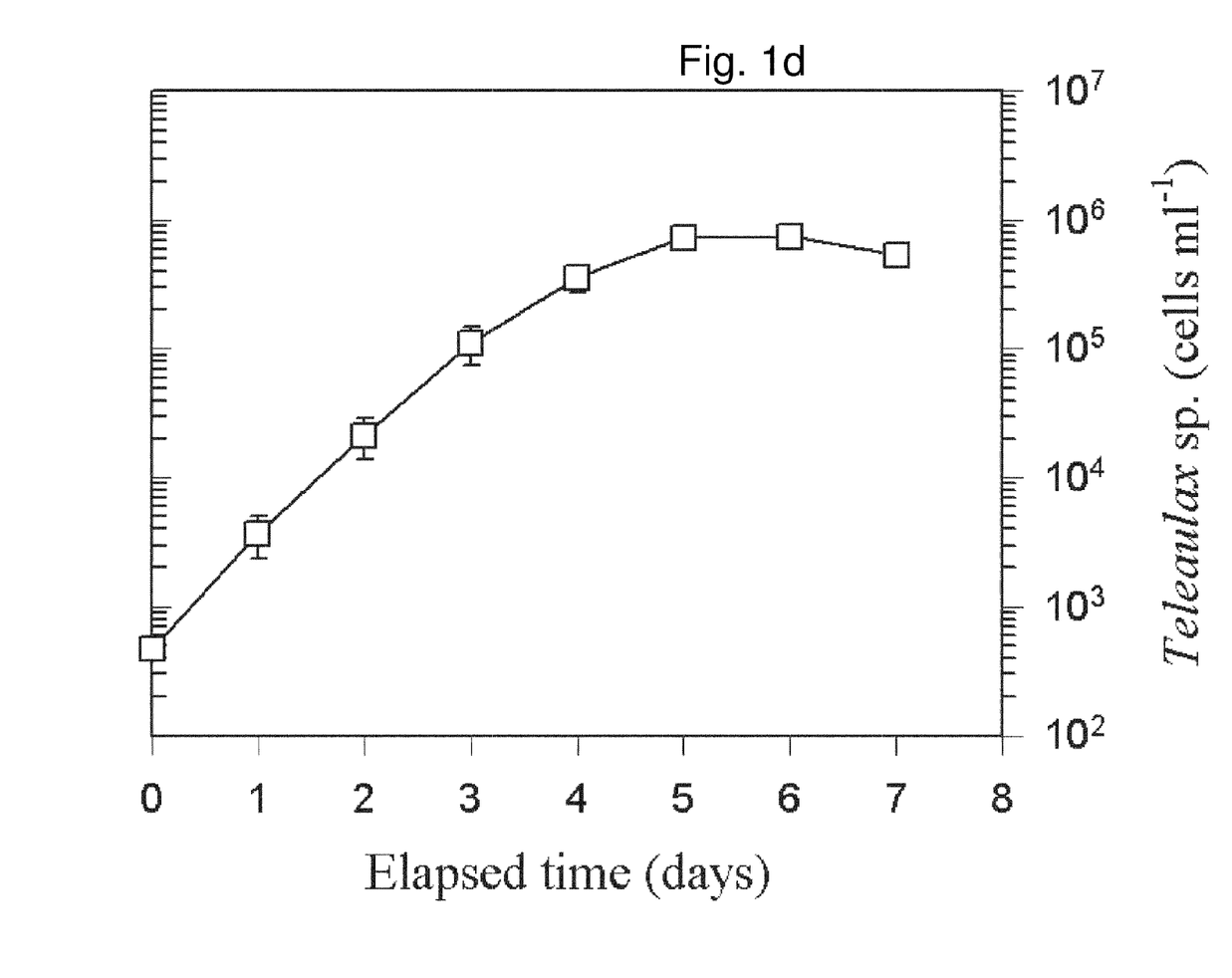
FIG. 1d is a graph showing change in cell number of Teleaulax sp. in cultures of Teleaulax sp. alone.

The results are shown in FIG. 1a. Data were shown as Mean± Standard Error of 3 replicate cultures. As shown in FIG. 1a, when offered Myrionecta rubra as prey, D. acuminata grew well with cell numbers remaining constant during the first day and increasing exponentially at a growth rate of 0.95 d$^{-1}$ (doubling time 17.5 h) over the next 3 d. After 4 d, initial M. rubra cells had declined by 97.5%, yet D. acuminata slowly continued to increase in numbers, reaching a maximum concentration of about 2400 cells·ml$^1$ at the end of the experiment.

COMPARATIVE EXAMPLES 1 to 6

Cultivation of Dinophysis Acuminata

In the above Example 1, M. rubra was cultured alone (Comparative Example 1); D. acuminata was cultured supplied with Teleaulax sp. as prey (Comparative Example 2); Teleaulax sp. was cultured alone (Comparative Example 3); D. acuminata was cultured alone without prey (Comparative Example 4); D. acuminata was cultured supplied with a mixture of M. rubra and Teleaulax sp. as prey (Comparative Example 5); and M. rubra and Teleaulax sp. were co-cultured without predator (Comparative Example 6). Initial cell densities of D. acuminata, M. rubra and Teleaulax sp. were 100, 500 and 500 cells·ml$^{-1}$, respectively. All bottles were incubated at 20° C. under continuous light (60 μmol photons·m$^-$$_2$·s$^{-1}$) for 7 d. Daily subsamples were fixed with acid Lugol's solution and cells were enumerated using a Sedgewick-Rafter chamber.

Figure 1E:
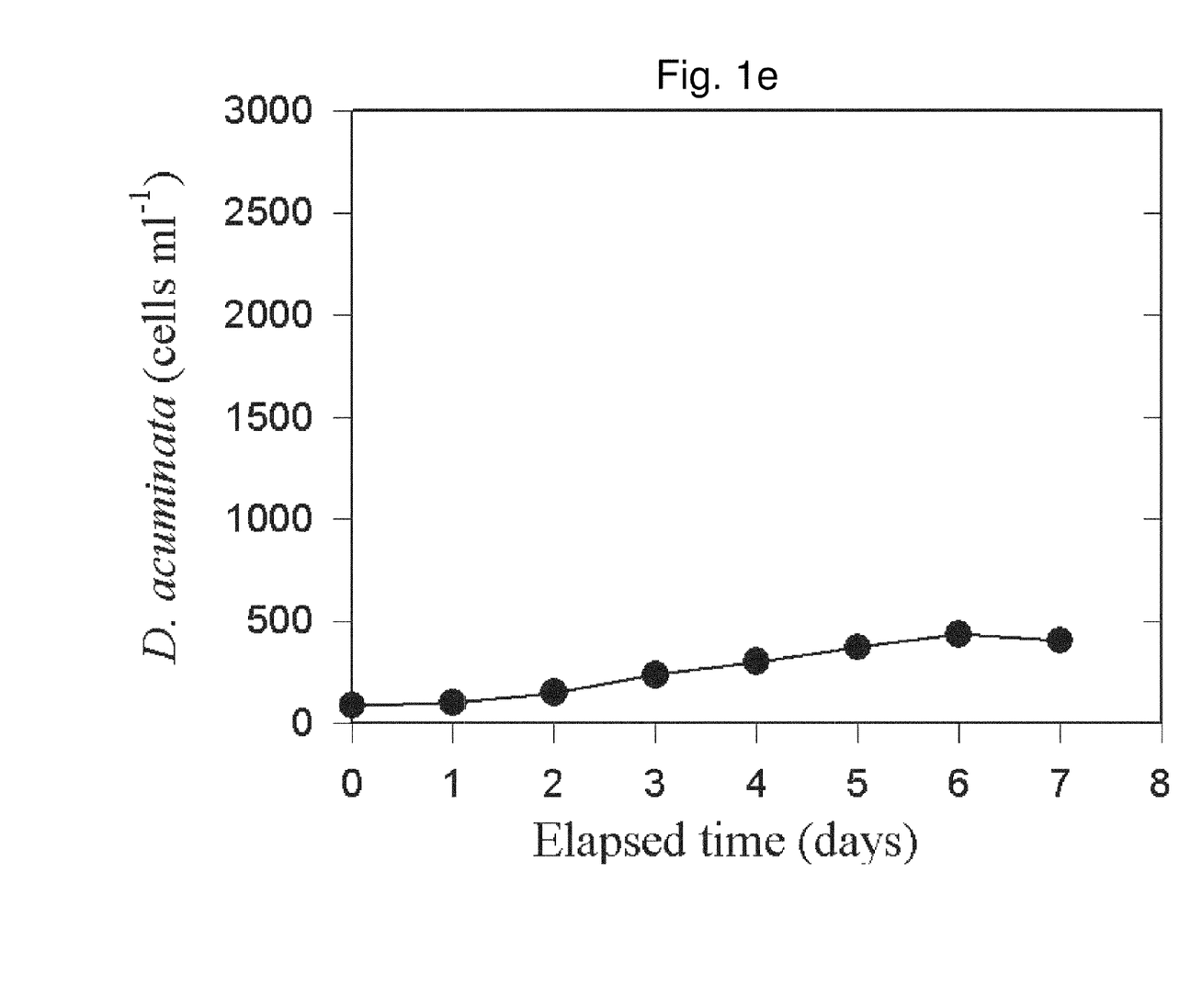
FIG. 1e is a graph showing change in cell number of D. acuminata in cultures of D. acuminata alone.
Figure 1F:
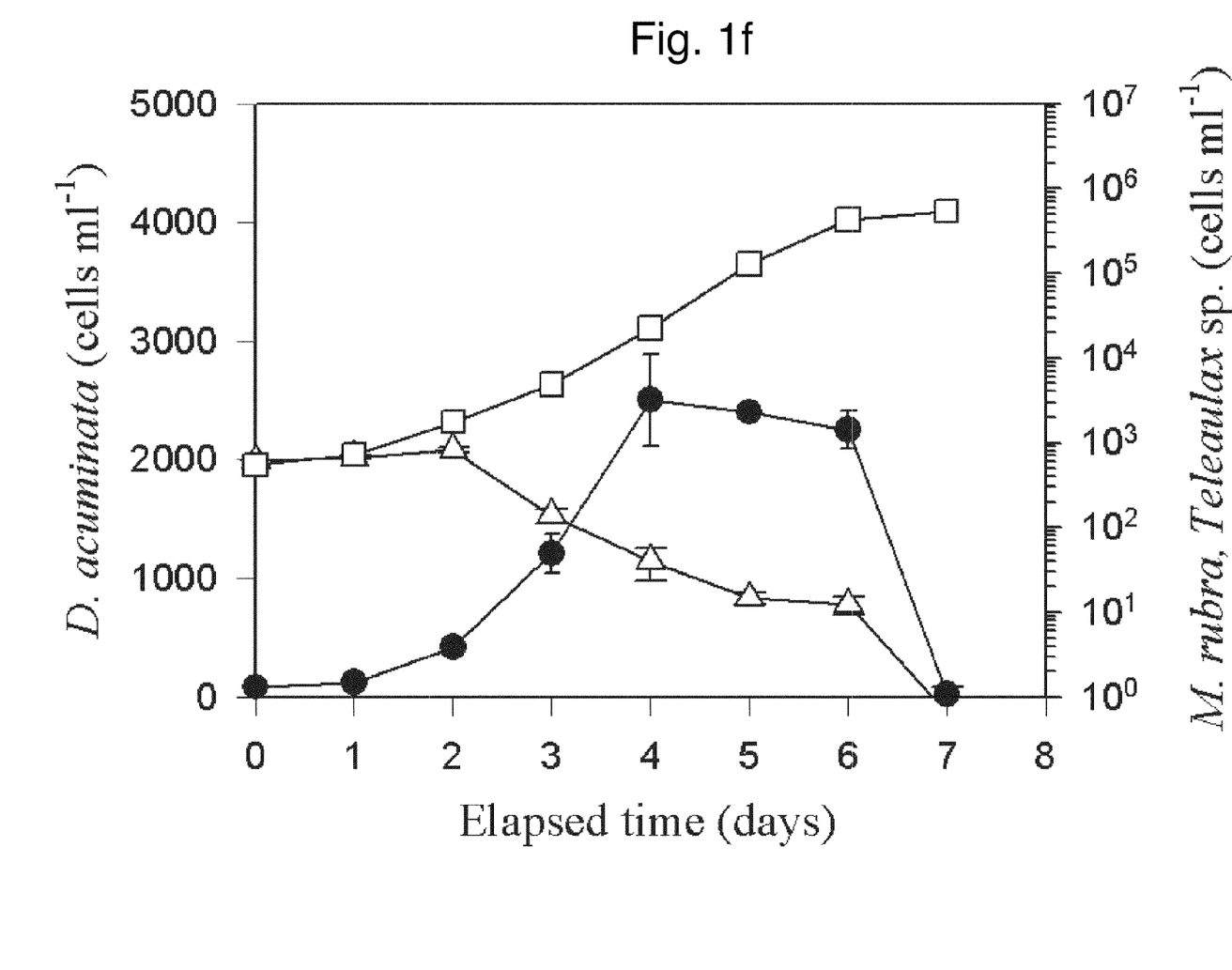
FIG. 1f is a graph showing changes in cell numbers of D. acuminata, M. rubra and Teleaulax sp. in cultures of D. acuminata supplied with both M. rubra and Teleaulax sp. as prey.
Figure 1G:
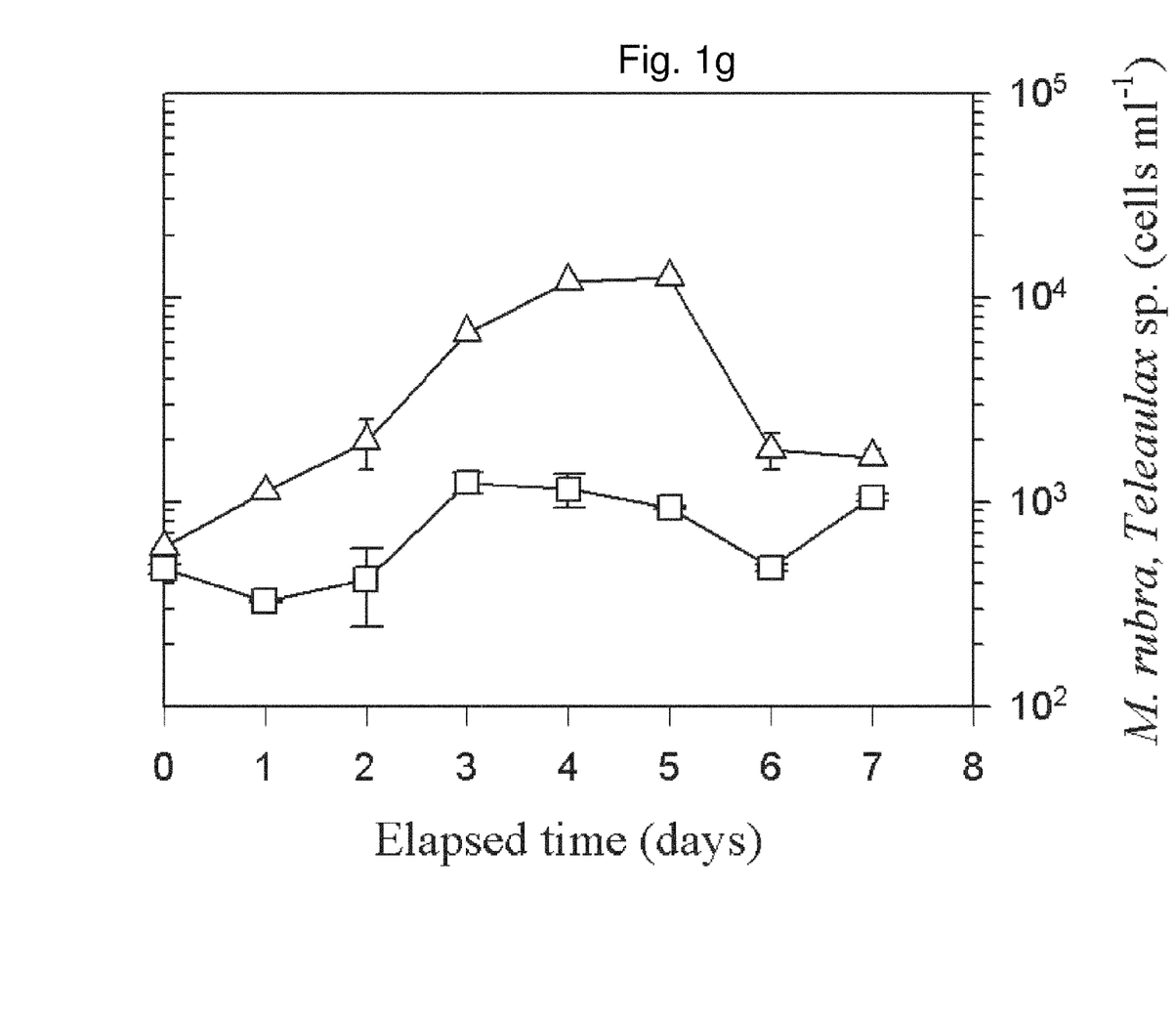
FIG. 1g is a graph showing changes in cell numbers of M. rubra and Teleaulax sp. in co-cultures of M. rubra and Teleaulax sp.

The results are shown in FIGS. 1b to 1g. Data were shown as Mean± Standard Error of 3 replicate cultures. As shown in FIGS. 1b to 1g, in bottles without the predators, M. rubra cell numbers increased exponentially with a growth rate of 0.61 d$^{-1}$ by Day 5, and remained constant thereafter (FIG. 1b: Comparative Example 1). When cryptophytes were offered as prey, D. acuminata cell numbers increased slightly to about 280 cells·ml$^{-1}$ (growth rate 0.31 d$^{-1}$) over the first 4 d and thereafter declined rapidly until the end of the experiment (FIG. 1c: Comparative Example 2). The slight initial increase in D. acuminata cell numbers in the presence of Teleaulax sp. did not appear to reflect growth supported by predation or kleptoplastidy, or both, on cryptophyte cells since growth of D. acuminata occurred at a similar rate (0.32 d$^{-1}$) in cultures without prey (FIG. 1e: Comparative Example 4). When grown with both M. rubra and Teleaulax sp., D. acuminata, cell numbers increased to about 2500 cells·ml$^{-1}$ over the first 4 d (growth rate of 0.91 d$^{-1}$), subsequently decreased slowly for 2 d, and then sharply declined to near zero values by the end of the experiment (FIG. 1f: Comparative Example 5). The sharp decline in *D. acuminata* after 6 d was accompanied by a parallel decline in *M. rubra* prey. The lack of ciliates, however, seems not to have been the primary cause for the decline in *D. acuminata* as this dinoflagellate is capable of surviving for many days in the absence of prey (FIG. 1e). A similar decline in *D. acuminata* was observed in bottles containing cryptophytes as potential prey (FIGS. 1c and 1f), which suggests that inhibition of *D. acuminata* growth was due to nutrient competition or allelopathy from *Teleaulax* sp. Another plausible explanation for the sharp decline in *D. acuminata* could be that the 3 species may differ in their pH limits for growth. The cryptophyte *Teleaulax* sp. may have a higher pH limit for growth compared with *M. rubra* or *D. acuminata*, and thus, these 2 species may reach their pH limits for growth before *Teleaulax* sp.

EXPERIMENTAL EXAMPLE 1

Observation of Feeding and Plastid Acquirement of *Dinophysis Acuminata*

Live observations of the feeding process were made on a glass slide using an Olympus BX51 microscope at 400× magnification and recorded with a Sony Progressive 3CCD color video camera attached to a digital imaging time-lapse recorder. For observations of plastid density and autofluorescence in *Dinophysis* cells, light and epifluorescence micrographs of live cells were taken at 1000× magnification using a digital camera (PowerShot G5, Canon) coupled to the Olympus BX51 microscope equipped with differential interference contrast and fluorescence cube (UMWB2, 450-480 nm excitation, 500 nm emission).

Figure 2:
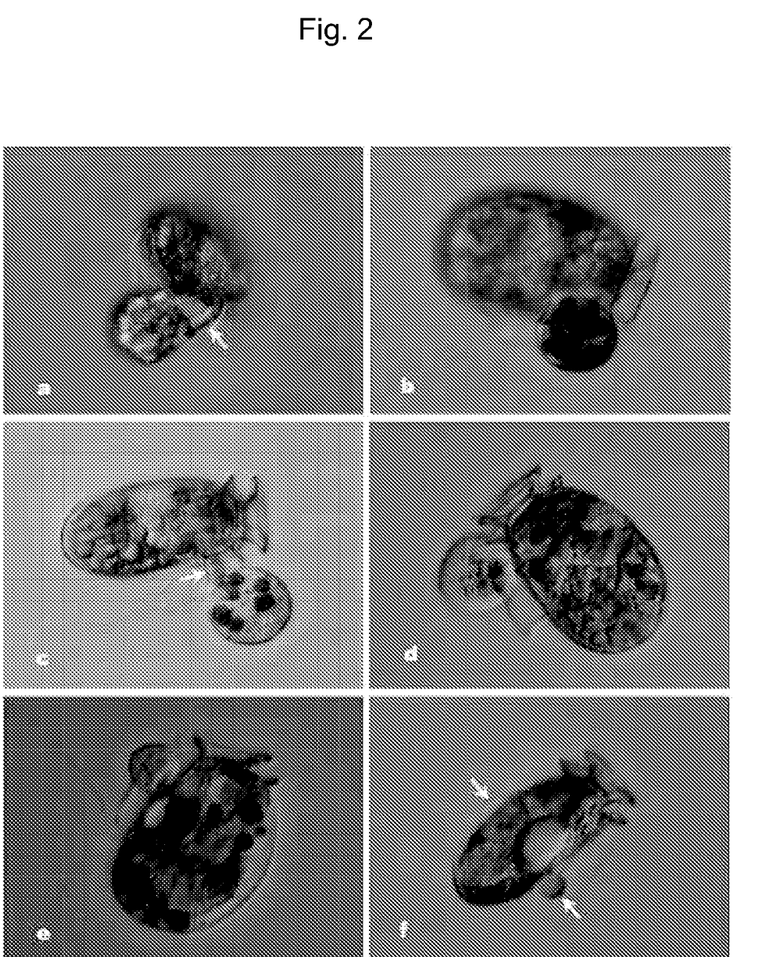
FIG. 2 ((a) to (f)) is a set of micrographs of D. acuminata feeding on M. rubra; and, FIG. 3 ((a) to (c)) is a set of light and epifluorescence micrographs of D. acuminata fed with M. rubra.
Figure 3:
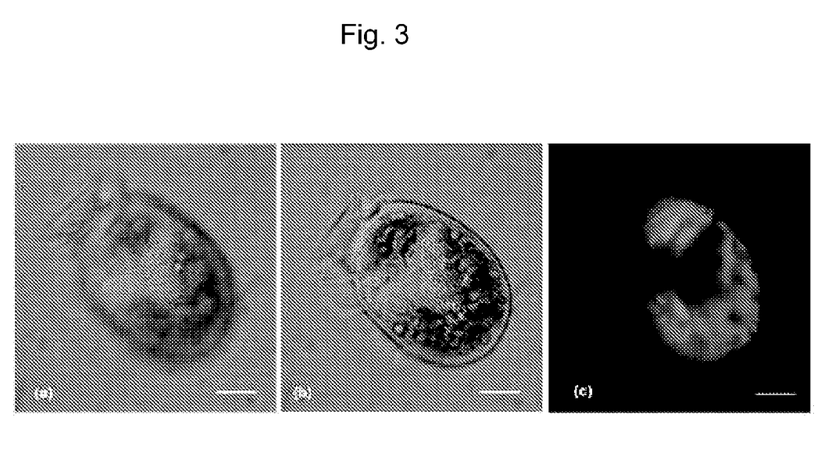

The results are shown in FIGS. 2 and 3, respectively. Microscopic observations of live cells using our established cultures revealed that *Dinophysis acuminata* uses a peduncle to extract the cell contents of the ciliate *Myrionecta rubra* (FIG. 2). While peduncle feeding has been reported for the heterotrophic species *D. rotundata* and *D. hastata*, the feeding mechanism used by photosynthetic or mixotrophic species of *Dinophysis* has not been previously observed. However, ultrastructure has revealed the presence of microtubular ribbons inside *D. acuminata* and *D. norvegica* that are presumably used during feeding. The precapture behaviour of *D. acuminata* differs from that of other marine thecate dinoflagellates (i.e. searching type) but is similar to that of the heterotrophic dinoflagellates *D. rotundata* and *D. hastata* (i.e. trapping type). The ciliate *M. rubra*, which has pronounced jumping behaviour, is captured by the dinoflagellate upon mechanical contact. After making physical contact, *D. acuminata* pierces *M. rubra* with a peduncle. Once trapped, the ciliate temporarily swims for about 1 min, towing the attached *D. acuminata*. However, the ciliate soon becomes immobile and the dinoflagellate then swims freely around towing the attached ciliate. At this time, *D. acuminata* starts to gradually consume the ciliate. During the early stage of feeding (i.e. capturing of prey and swimming), most cilia are shed from the body of *M. rubra* (FIGS. 2a and 2b). During feeding, *D. acuminata* extracts the contents of the prey using the peduncle that extends from the flagellar pore. During the last stage of the feeding process, which lasts for about 1 to 2 h, the *D. acuminata* cell is filled with vacuoles containing ciliate cytoplasm (FIGS. 2d and 2e). In addition, plastids were frequently noticed within the cytoplasm of *D. acuminata* (FIGS. 3a and 3b). Epifluorescence microscopy revealed that *D. acuminata* emitted bright yellow-orange fluorescence under blue light excitation (FIG. 3c, bar=10 μm), typical of cryptophycean phycobilin (phycoerythrin). After the feeding event, *D. acuminata* was frequently observed with balloonlike spheres (arrows) of varying size distributed close to the cell surface (FIG. 2f).

As *M. rubra* gets plastids from *Teleaulax* sp., *D. acuminata* may get its plastids as kleptoplastidy from ingesting *M. rubra*. Therefore, the plastids would be secondary kleptoplastids if the argument that *M. rubra* gets plastids from *Teleaulax* sp. by kleptoplastidy is correct. If, however, the argument that *M. rubra* eats *Teleaulax* sp. for obtaining an essential growth factor for continued growth is correct, then the plastids of *D. acuminata* would be primary kleptoplastids. Alternatively, *D. acuminata* may have its own plastids and simply eat *M. rubra* to acquire some essential growth factor.

Industrial Applicability

The present invention has first established a method for cultivating *D. acuminata* in laboratory whose cultivation was known difficult, based on the interactions among three species, *D. acuminata, M. rubra* and *Teleaulax* sp. The present invention would contribute to a better understanding of ecophysiology, biology and toxicology of *Dinophysis* species, as well as the evolution of dinoflagellate plastids.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for cultivating *Dinophysis acuminata*, comprising the step of cultivating *Dinophysis acuminata* in a seawater medium at a temperature of 10-30° C. under continuous light, wherein the medium contains *Myrionecta rubra* as a food source.

2. The method for cultivating *Dinophysis acuminata* according to claim 1, wherein the medium does not contain *Teleaulax* sp.

3. The method for cultivating *Dinophysis acuminata* according to claim 1, wherein the seawater medium is f/2-Si medium.

4. The method for cultivating *Dinophysis acuminata* according to claim 1, wherein initial density ratio of *Dinophysis acuminata* to *Myrionecta rubra* is 1:1-10.

5. The method for cultivating *Dinophysis acuminata* according to claim 1, wherein the cultivation is performed under continuous light of 50-100 μmol photon·m$^{-2}$·s$^{-1}$.

* * * * *